US012773523B2

(12) United States Patent
Panesar et al.

(10) Patent No.: US 12,773,523 B2
(45) Date of Patent: Oct. 27, 2026

(54) SMART METER FOR CATHETER HYDRATION AND INSERTION

(71) Applicant: Hollister Incorporated, Libertyville, IL (US)

(72) Inventors: Satwinder S. Panesar, Foxford (IE); David J. Farrell, Ballina (IE)

(73) Assignee: Hollister Incorporated

( * ) Notice: Subject to any disclaimer, the term of this patent is extended or adjusted under 35 U.S.C. 154(b) by 864 days.

(21) Appl. No.: 18/041,787

(22) PCT Filed: Jul. 22, 2021

(86) PCT No.: PCT/US2021/042689
§ 371 (c)(1),
(2) Date: Feb. 15, 2023

(87) PCT Pub. No.: WO2022/039880
PCT Pub. Date: Feb. 24, 2022

(65) Prior Publication Data
US 2024/0024620 A1 Jan. 25, 2024

Related U.S. Application Data

(60) Provisional application No. 63/067,650, filed on Aug. 19, 2020.

(51) Int. Cl.
*A61M 25/00* (2006.01)
*A61M 25/01* (2006.01)

(52) U.S. Cl.
CPC ..... *A61M 25/0017* (2013.01); *A61M 25/0111* (2013.01)

(58) Field of Classification Search
CPC .......... A61M 25/0017; A61M 25/0111; A61M 2210/1078; A61M 2210/1089; A61M 25/0113; A61M 27/00; A61M 39/00; A61M 5/00; A61M 25/09041; A61F 5/453; A61B 34/00; A61B 2034/301
See application file for complete search history.

(56) References Cited

U.S. PATENT DOCUMENTS 3,794,042 A 2/1974 De Klotz et al.
4,657,486 A * 4/1987 Stempfle ................ F04B 49/02 604/153

(Continued)

FOREIGN PATENT DOCUMENTS

WO 2005092418 A1 10/2005
WO 2012037213 A1 3/2012

OTHER PUBLICATIONS

International Search Report and Written Opinion for International Application No. PCT/US2021/042689 Dated Nov. 17, 2021.

*Primary Examiner* — Bhisma Mehta
*Assistant Examiner* — Fatimata Sahra Diop
(74) *Attorney, Agent, or Firm* — Cook Alex Ltd.

(57) ABSTRACT

A smart meter for catheter hydration and insertion, including a housing that receives a catheter, and a fluid reservoir that connects to the housing. A catheter hydration chamber, a pump and a drive system are located within the housing. The pump is in communication with the fluid reservoir and the hydration chamber. The drive system includes a motor and a drivetrain that engages and moves the catheter.

20 Claims, 13 Drawing Sheets

(56) References Cited

U.S. PATENT DOCUMENTS

| | | | | |
|---|---|---|---|---|
| 5,176,647 | A * | 1/1993 | Knoepfler | A61M 25/0113 604/181 |
| 5,586,968 | A * | 12/1996 | Grundl | A61B 1/31 600/114 |
| 6,077,219 | A | 6/2000 | Viebach et al. | |
| 6,319,227 | B1 | 11/2001 | Mansouri-Ruiz | |
| 6,726,675 | B1 | 4/2004 | Beyar | |
| 6,974,465 | B2 | 12/2005 | Belef et al. | |
| 7,393,501 | B2 | 7/2008 | Zumeris et al. | |
| 8,104,479 | B2 | 1/2012 | Glynn et al. | |
| 9,662,058 | B2 | 5/2017 | Burnett et al. | |
| 2002/0107478 | A1 | 8/2002 | Wendlandt | |
| 2003/0139701 | A1 * | 7/2003 | White | A61M 5/142 604/67 |
| 2015/0133963 | A1 | 5/2015 | Barbagli | |
| 2016/0310222 | A1 | 10/2016 | Kottenstette | |
| 2017/0086746 | A1 | 3/2017 | Ofek et al. | |
| 2018/0177458 | A1 | 6/2018 | Burnett et al. | |
| 2019/0328915 | A1 | 10/2019 | Paul et al. | |
| 2020/0246603 | A1 * | 8/2020 | Isaacson | A61M 39/20 |
| 2020/0375682 | A1 * | 12/2020 | Kincaid | A61B 34/71 |
| 2021/0069473 | A1 * | 3/2021 | Marass | A61M 25/0662 |

* cited by examiner

SMART METER FOR CATHETER HYDRATION AND INSERTION

CROSS-REFERENCE TO RELATED APPLICATION

This application is the U.S. National Stage Application of PCT Application No. PCT/US2021/042689, filed Jul. 22, 2021, which claims the benefit of U.S. Provisional Patent Application Ser. No. 63/067,650, filed Aug. 19, 2020, the disclosure of all of which is hereby incorporated by reference in its entirety.

FIELD OF THE DISCLOSURE

The present disclosure is directed to medical devices involving catheters. More particularly, the present disclosure is directed to systems for hydrating and inserting urinary catheters. The systems include a smart meter that may be used to control hydration, insertion and retraction of a urinary catheter.

BACKGROUND

Catheters may be used by individuals who suffer from abnormalities of the urinary system, such as urinary incontinence, or who may have a temporary need for relatively frequent catheterization. The catheters may be intermittent catheters that commonly have a connector or funnel at a proximal end and an elongated shaft that terminates in a catheter tip at an opposed distal end. The connector and shaft include a passage that is in communication with at least one aperture through the catheter tip.

Individuals may need to self-catheterize, by undergoing self-insertion and self-removal of a catheter several times a day. Use of intermittent catheters may occur at home or, for example, in a public restroom. The catheter tip is inserted into and through the urethra to access and drain urine from the individual's bladder, through the catheter and into a waste receptacle, such as a toilet or collection bag. It can be challenging for some individuals to properly manage to prepare a catheter for insertion, and to handle the catheter during insertion and removal.

SUMMARY

The present disclosure is directed to a smart meter for catheter hydration and insertion, including a housing that receives a catheter, and a fluid reservoir that connects to the housing. A catheter hydration chamber, a pump and a drive system are located within the housing. The pump is in communication with the fluid reservoir and the hydration chamber. The drive system includes a motor and a drivetrain that engages and moves the catheter.

The smart meter provides enhanced convenience, safety and control of the catheter hydration and insertion process. The smart meter also may be used to control removal of the catheter and ultimately significantly improves the process of self-catheterization using intermittent catheters.

Smart meters may be bespoke, in the sense of being configured for use with specific catheters, such as catheters supplied by a specific manufacturer and/or being of a specific model. Moreover, the smart meters may include or be used with a catheter identification device, such as a scanner or bar code reader, to identify whether such a compatible catheter is being used.

It will be appreciated that the smart meter for hydration and insertion of a catheter may be used with the controller to control or adjust aspects involving hydration, insertion and removal of the catheter. The smart meter controller may include a user interface and may utilize artificial intelligence (AI) functionality.

BRIEF DESCRIPTION OF THE DRAWINGS

In describing the preferred embodiments, reference is made to the accompanying drawing figures wherein like parts have like reference numerals, and wherein.

Figure 2:
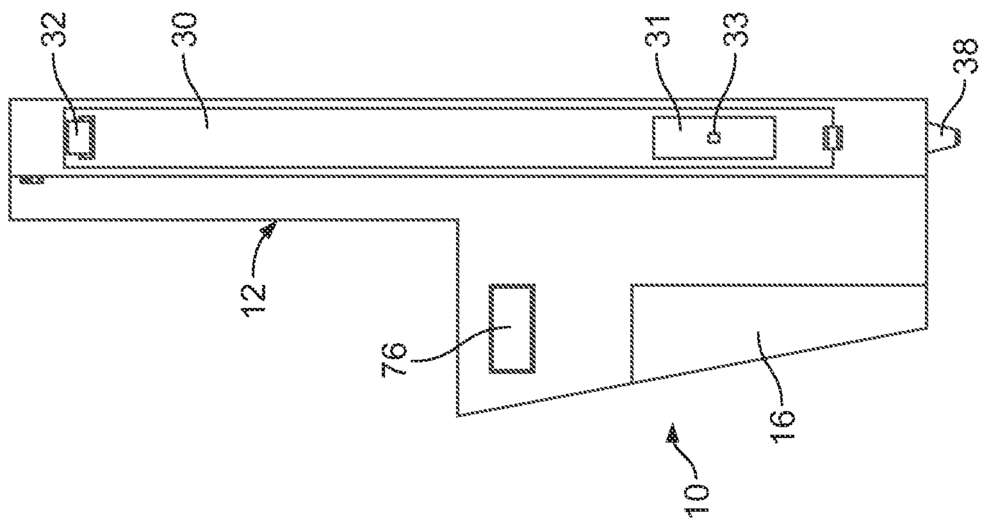
FIG. 2 is a top view of the smart meter of FIG. 1.
Figure 1:
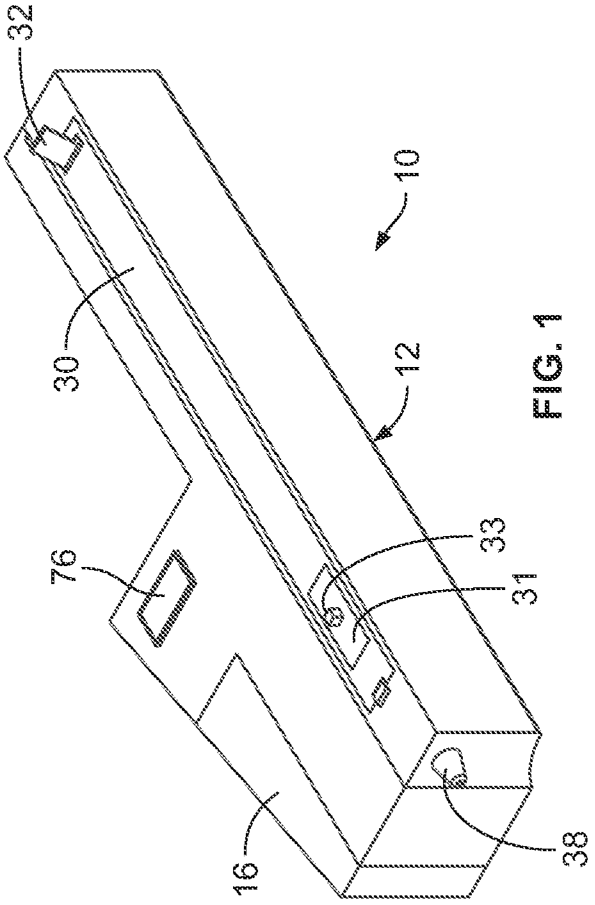
FIG. 1 is a front upper perspective view of a first example smart meter for hydration and insertion of a catheter.
Figure 3:
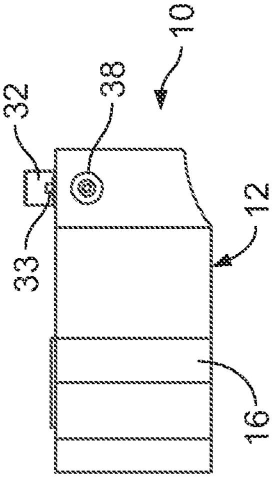
FIG. 3 is a front view of the smart meter of FIG. 1.
Figure 4:
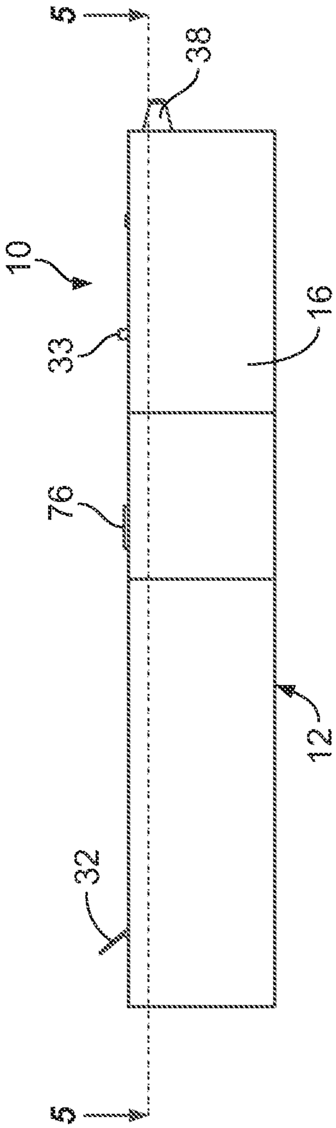
FIG. 4 is a side view of the smart meter of FIG. 1, identifying a section 5-5, which is shown in FIG. 5.

It should be understood that the drawings are not to scale. While some mechanical details of example smart meters for hydration and insertion of a catheter, including other plan and section views of the particular components, have not been shown, such details are considered to be within the comprehension of those skilled in the art in light of the present disclosure. It also should be understood that the present disclosure and claims are not limited to the preferred embodiments illustrated.

DETAILED DESCRIPTION OF THE EMBODIMENTS

The present disclosure provides examples of systems for hydrating and inserting urinary catheters. The examples are shown in FIGS. 1-29 and described herein as including a smart meter that may be used to control hydration, insertion and retraction of a urinary catheter. The smart meter optionally may be used to sterilize the catheter prior to insertion.

For instance, a first example smart meter for catheter hydration and insertion 10 is shown in FIGS. 1-18. As may be seen in FIGS. 1-8, the smart meter 10 includes a housing 12 that receives a catheter 14, and a fluid reservoir 16 that connects to the housing 12. A catheter hydration chamber 20, a pump 22 and a drive system 24 are located within the housing 12. The pump 22 is in communication with the fluid reservoir 16 and the hydration chamber 20. The drive system 24 includes a motor 26 and a drivetrain 28 that engages and moves the catheter 14. It will be understood that the catheter 14 may be of different configurations but typically will include a connector 14*a*, such as in the form of a funnel, a catheter shaft 14*b* having a passage therethrough, and a catheter tip 14*c* having at least one aperture to permit fluid communication through the catheter 14 from the tip 14*c* to the connector 14*a*. The catheter 14 may be a hydrophilic catheter that includes a hydrophilic coating that becomes lubricious when wetted or hydrated with a hydration liquid. The lubricious hydrophilic coating eases insertion and withdrawal of the catheter from the urethra.

The housing 12 includes a cover or lid 30 that closes and seals the hydration chamber 20. A lift tab 32 is provided to conveniently grasp and open the lid 30 to access the hydration chamber 20, thereby allowing a user to insert or remove a catheter 14 from the hydration chamber 20. The fluid reservoir 16 may be reusable and filled prior to use, or a disposable prefilled item. The fluid reservoir 16 may have a suitable volume, for instance a volume of 2-10 ml or more, but will depend upon the hydration mechanism utilized and the volume of the hydration chamber 20. The fluid reservoir 16 may be conveniently connected to or removed from the housing 12, as may be seen in FIGS. 9-11. For instance, the example smart meter 10 includes reservoir connectors 34 in the form of locking ridges that are slidably received by housing connectors 36 in the form of slots on the housing 12.

The housing 12 also has an introducer tip 38 at a distal end of the housing and through which the distal end or tip 14*c* and catheter shaft 14*b* are extendable, so as to provide for insertion of the catheter 14 into the individual. The introducer tip 38 may be self-sealing and/or adjustable to accommodate catheter shafts 14*b* of different diameters. The introducer tip 38 also may be adjustable to accommodate all sizes of urethra openings and may utilize fluid from the fluid reservoir 16 to be self-cleaning. Still further, the introducer tip may contain lubricant to provide catheter lubricity during extension of the catheter through the introducer tip. Thus, the introducer tip may include a small reservoir that is loaded with lubricant to improve catheter lubricity and/or to be used with uncoated catheter tubes that could be lubricated as they are extended through the introducer tip.

When in use for catheterization, the motor 26 and drivetrain 28 of the drive system 24 move the catheter 14 relative to the housing 12 in a first direction for catheter insertion and in an opposed second direction for catheter removal. In the example smart meter 10, the drivetrain 28 utilizes rotary motion to move the catheter 14. As may be seen in FIGS. 5-6, 8 and 13-16, the rotary motion of the drivetrain 28 begins with a rotation of a drive gear 40 on the motor 26. The drive gear 40 rotates an input gear 42 on a first end of a rotatable gear shaft 44. The rotatable gear shaft 44 has an output gear 46 on an opposed second end. The output gear 46 rotates an idler gear 48, which is rotatably received in a holder 50 on the housing 12. The idler gear 48 rotates an input gear 52 of a screw drive assembly 54. The screw drive assembly 54 includes a screw shaft 56 that is connected to the input gear 52. A catheter holder or carriage 58 has a through bore that is shaped to be complementary to the thread or coil shape along the screw shaft 56. As such, the carriage 58 engages and moves along the screw shaft 56 when the screw shaft 56 is rotated. To ensure the carriage 58 translates relative to the rotatable screw shaft 56, the carriage 58 has a passage 60 that slidably receives a carriage guide shaft 62. The carriage guide shaft 62 is supported at a proximal first end by a stabilizer 64 that extends from the housing 12. The carriage guide shaft 62 is held at a distal second end by a stop block 66 that is connected to a distal end of the housing 12. The stop block 66 includes a socket 68 that receives the distal end of the rotatable screw shaft 56.

Figure 6:
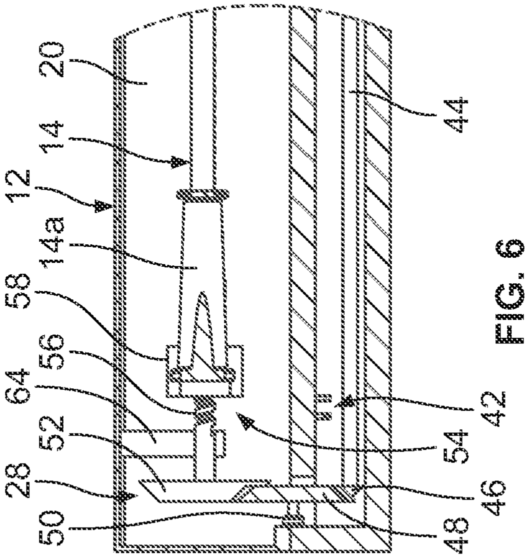
FIG. 6 is an enlarged cross-sectional top view of the designated detail area in FIG. 5.
Figure 7:
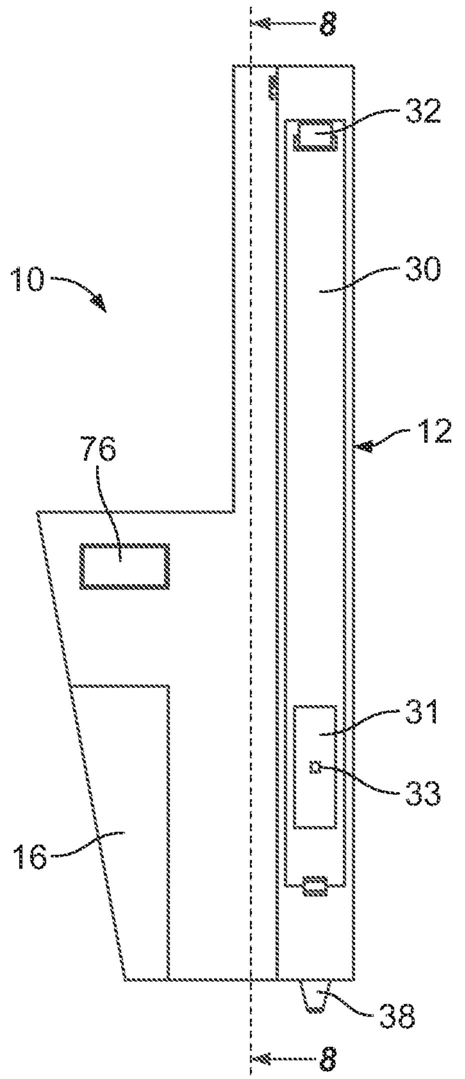
FIG. 7 is a top view of the smart meter of FIG. 1, identifying a section 8-8, which is shown in FIG. 8.
Figure 14:
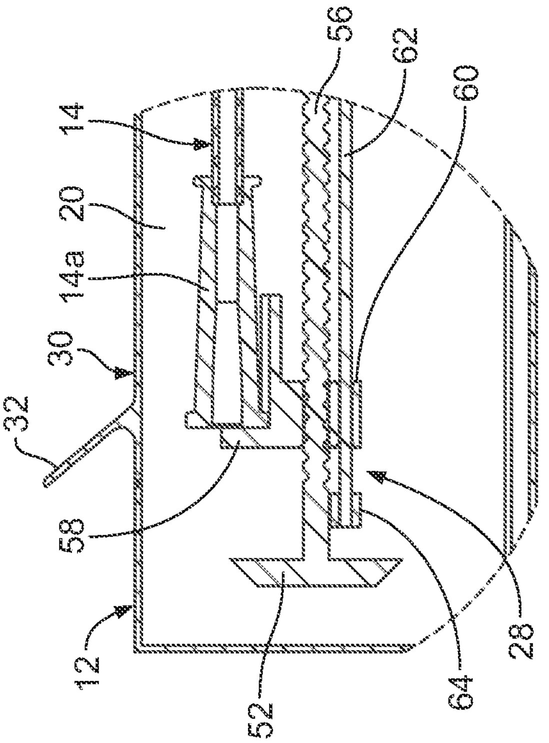
FIG. 14 is an enlarged cross-sectional side view of the designated detail area shown in FIG. 13.
Figure 15:
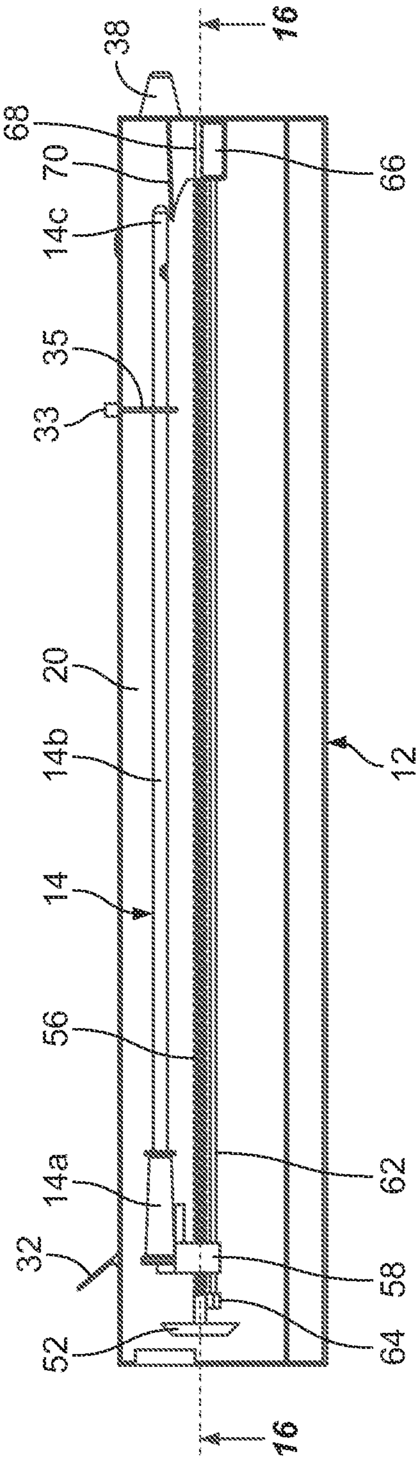
FIG. 15 is a side view of the catheter chamber portion of the smart meter of FIG. 12, identifying a section 16-16, which is shown in FIG. 16.
Figure 16:
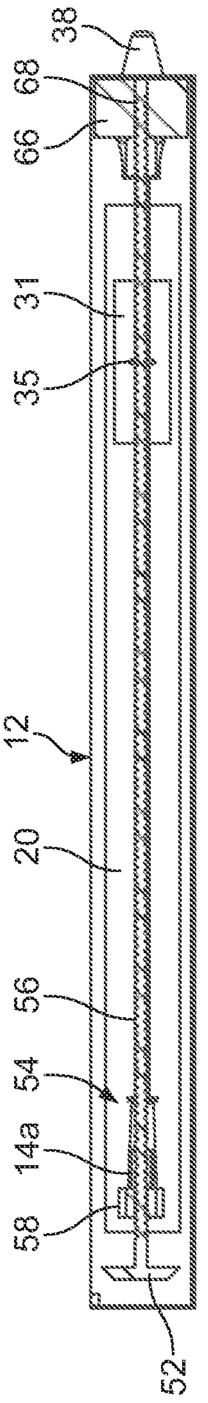
FIG. 16 is a cross-sectional top view of the smart meter at section 16-16 of FIG. 15.
Figure 17:
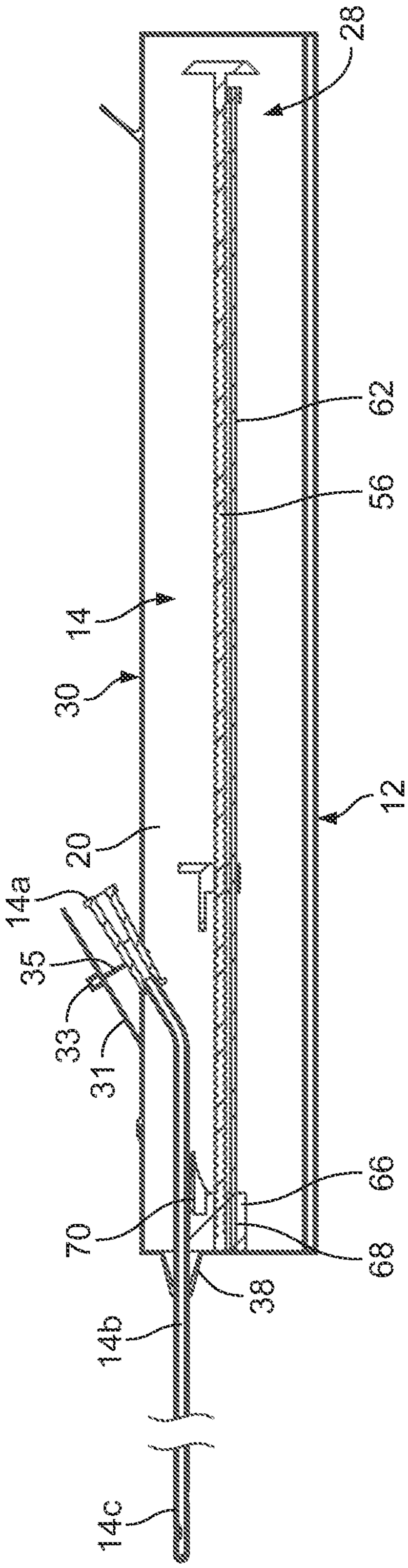
FIG. 17 is a side view of the catheter chamber portion of the smart meter of FIG. 12, identifying a section 18-18, which is shown in FIG. 18, and with the catheter fully extended and the catheter connector accessible.
Figure 18:
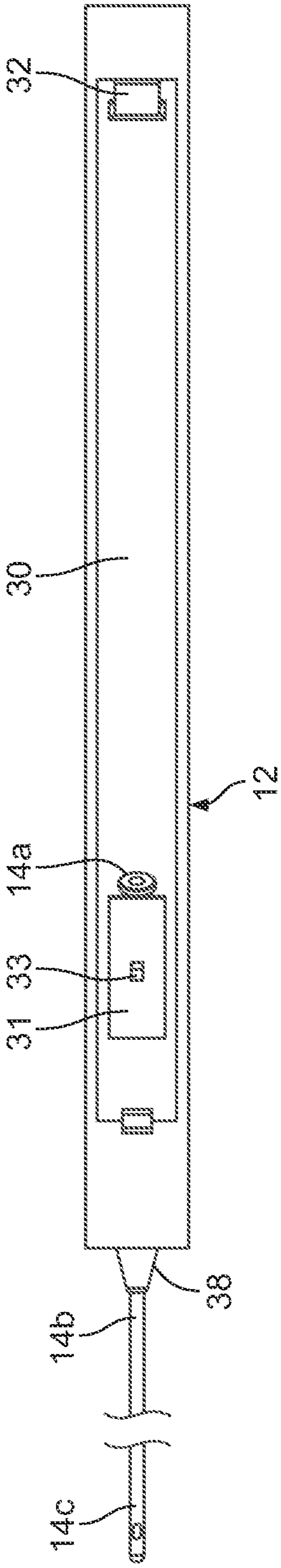
FIG. 18 is a cross-sectional top view of the smart meter at section 18-18 of FIG. 17.
Figure 19:
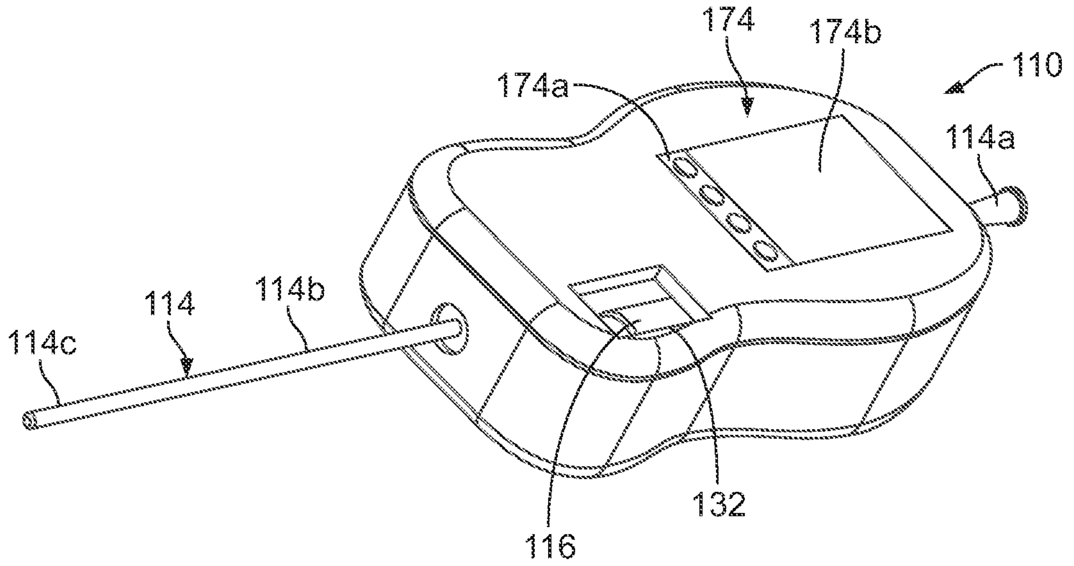
FIG. 19 is a front upper perspective view of a second example smart meter for hydration and insertion of a catheter.
Figure 20:
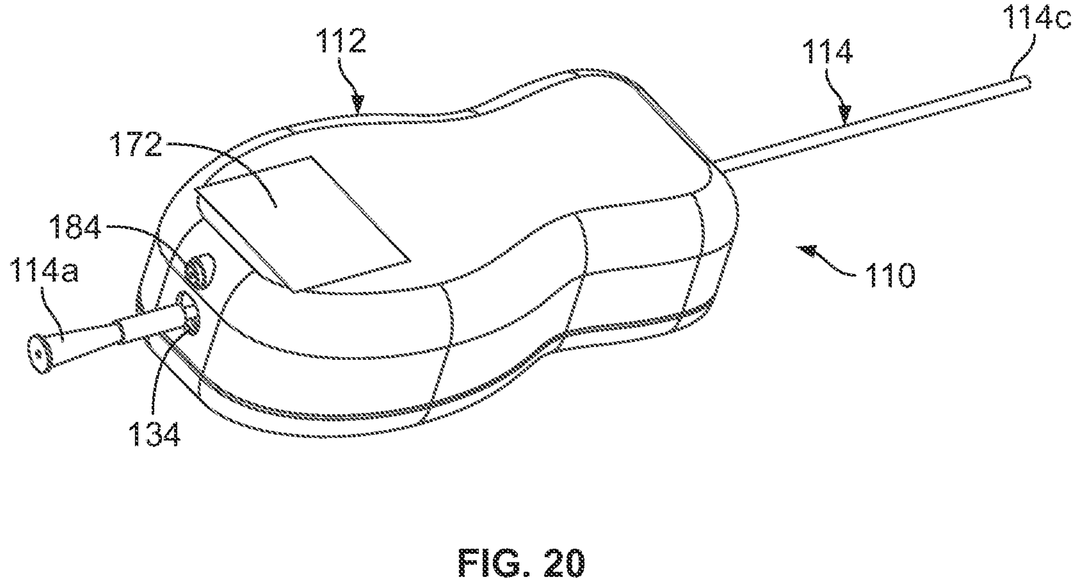
FIG. 20 is a rear upper perspective view of the smart meter of FIG. 19.
Figure 21:
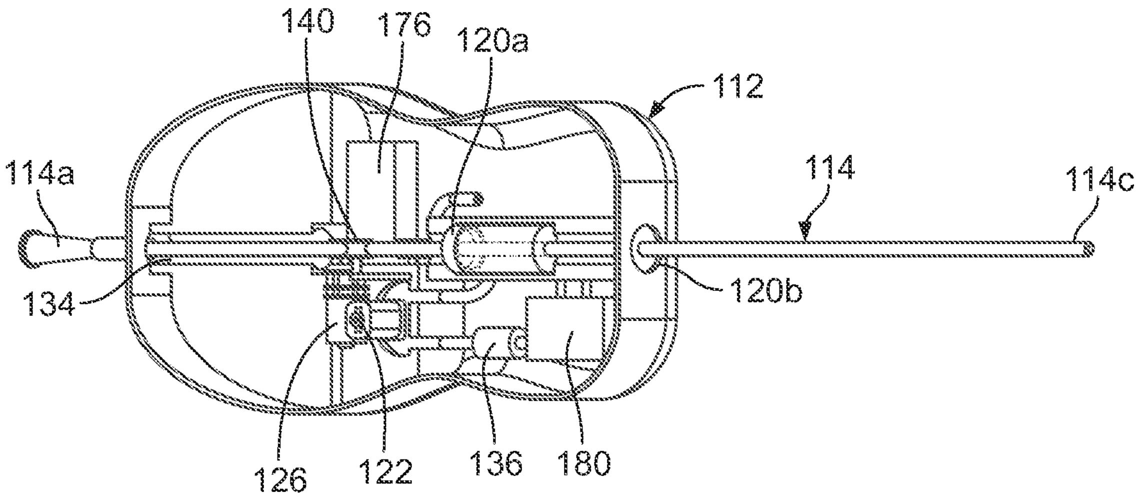
FIG. 21 is an upper perspective view of the smart meter of FIG. 19, with a front cover removed and showing inside of the housing with the hydration chamber removed for ease of viewing.
Figure 22:
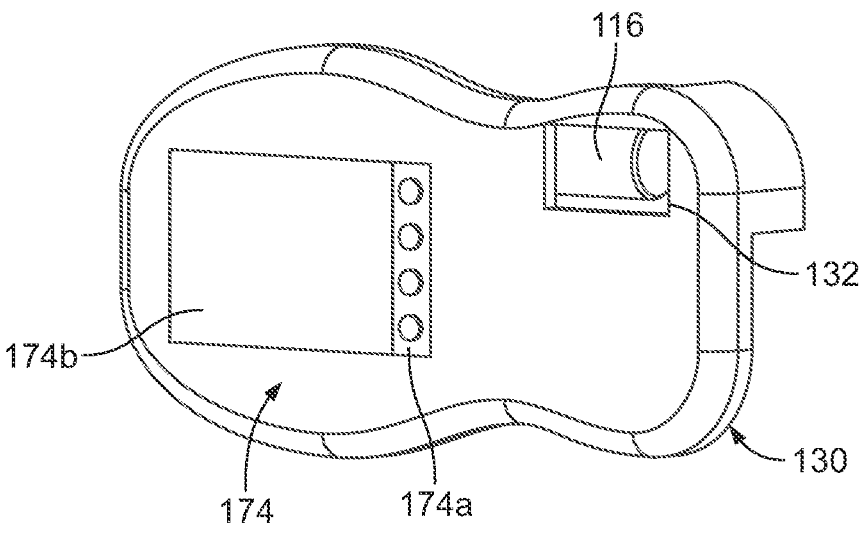
FIG. 22 is an upper perspective view of the front cover of smart meter of FIG. 19.
Figure 23:
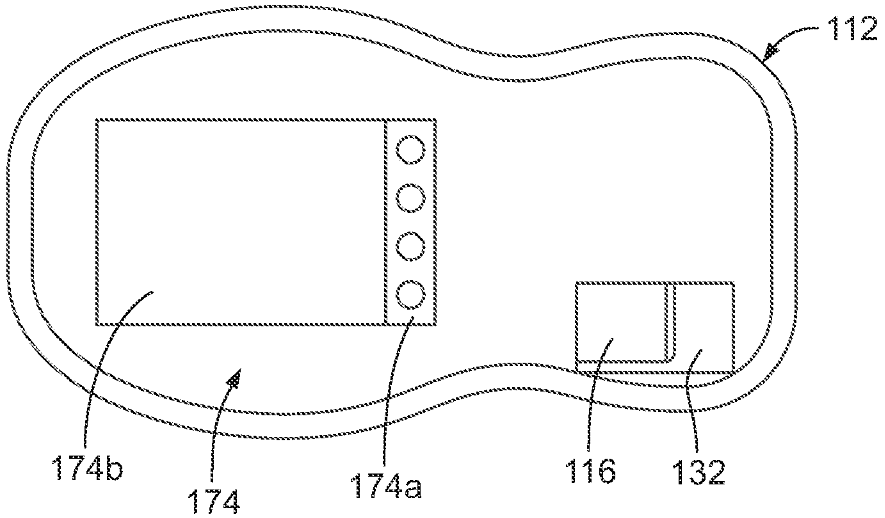
FIG. 23 is a top view of the front cover of the smart meter of FIG. 19.
Figure 24:
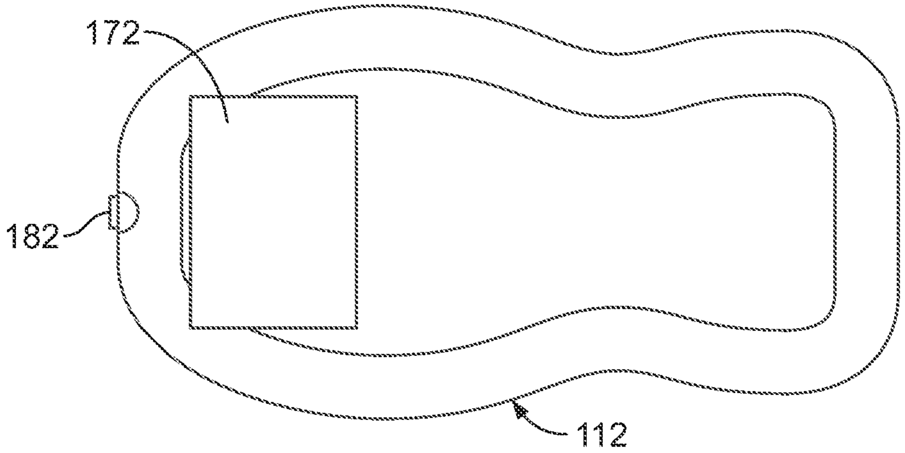
FIG. 24 is a bottom view of the smart meter of FIG. 19.

As may be seen in FIGS. 6, 14 and 15, this configuration has the screw shaft 56 supported for rotation by the carriage 58, which in turn is supported by and slides along the carriage guide shaft 62. Thus, the screw shaft 56 is supported above and parallel to the carriage guide shaft 62. The stop block 66 also includes a catheter guide surface 70 to assist in guiding the catheter tip 14*c* through the introducer tip 38.

Figure 8:
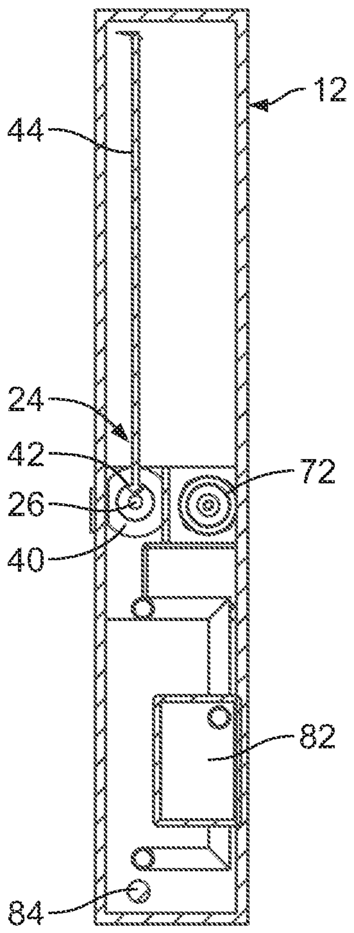
FIG. 8 is a cross-sectional side view of the smart meter at section 8-8 of FIG. 7.
Figure 10:
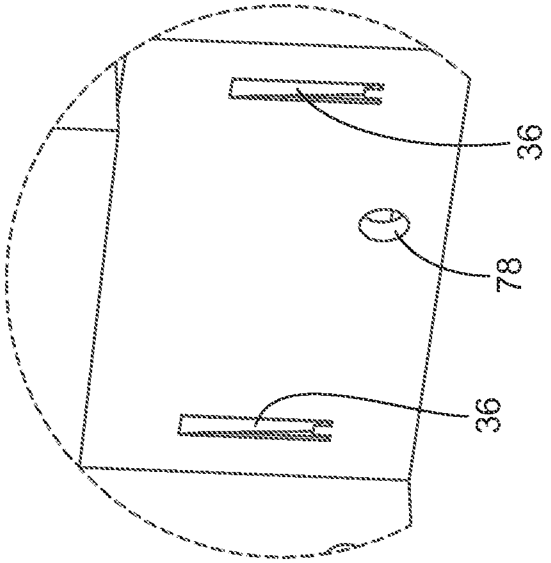
FIG. 10 is an enlarged front side perspective view of the designated detail area in FIG. 9.
Figure 11:
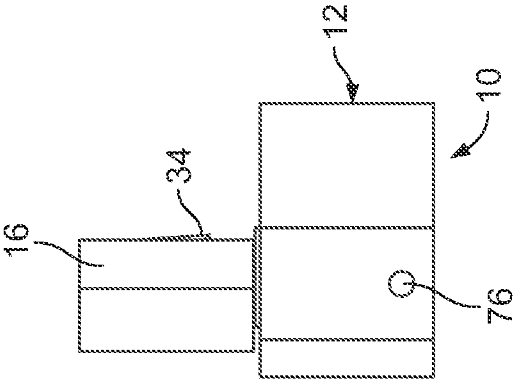
FIG. 11 is a front view of the smart meter with the fluid reservoir in the position shown in FIG. 9.
Figure 9:
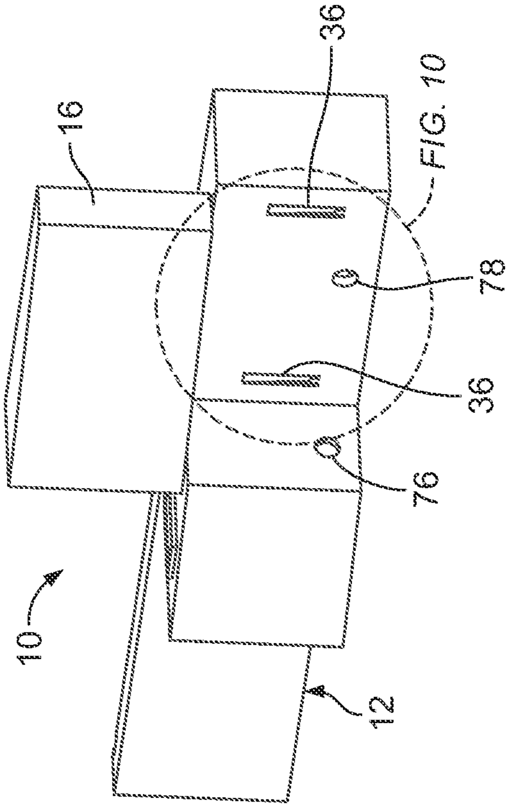
FIG. 9 is a front side perspective view of the smart meter of FIG. 1 showing the fluid reservoir disconnected from the housing and noting a designated detail area shown in FIG. 10.

The smart meter 10 includes a power source 72, which is best seen in FIG. 8 and may be in the form of one or more rechargeable batteries. The power source 72 provides power to the pump 22 and motor 26, as well as to an operator interface and controller 74. The operator interface and controller 74 may provide on the housing 12 input mechanisms, such as membrane switches, buttons, a touch screen or the like, as well as a readout, such as an LCD display or the touch screen and may be provided in the form of a graphical user interface (GUI). The controller may include an onboard microprocessor or computer. It will be appreciated that the operator interface and controller may be configured as an integrated unit, or an operator interface may be located on the housing and a controller may be in communication with the operator interface but separately located within the housing 12. The operator interface and controller 74 also may be programmed to utilize smart features, such as are provided when using a modern handheld cellular telephone. It also may be configured to communicate with a separate device, such as a computer, tablet computer for cellular telephone.

The operator interface and controller 74 may include artificial intelligence capabilities. For example, AI may provide software including a system to read identifying indicia on catheters for use in the device, such as bar codes, and to analyze data and assist in controlling the speed of catheter movement. The speed may be varied based on frictional data collected. For instance, if during catheter insertion the frictional data is higher than normal or than would be desirable, the AI system may cause the drive system to move more slowly to reduce the insertion rate, so as to avoid causing pain. There may be a determined or preset threshold or alert level for frictional force which, if exceeded, causes the insertion process to stop and/or reverse to withdraw the catheter. The AI functionality may be utilized to better control hydration of the catheter and ease of insertion and withdrawal of the catheter. Thus, the smart meter may include an AI system that makes decisions based on parameters that are measured by sensors, so as to improve the control and comfort attainable with the device.

The lid 30 also includes an access hatch 31 located closer to the introducer tip 38. The access hatch 31 includes a pull tab 33 on the exterior and a catheter holder 35 that extends from the underside. The access hatch 31 pivots upward from the lid 30 while the lid 30 is closed, such as to roughly a 60 degree angle when the access hatch 31 is opened. The catheter holder 35 extends below the catheter 14, and when the catheter is advanced and extended from the device 10, the catheter holder 35 extends below the connector 14*a*, which his shown as a funnel. Thus, once the catheter has been extended, the connector 14*a* may be conveniently accessed by grasping the pull tab 33 and opening the access hatch 31, which in turn has the catheter holder 35 lift the catheter connector 14*a* outward to permit drainage. It will be appreciated that the access hatch 31 may be provided separately from the lid 30, if the lid 30 is shorter in length.

Figure 5:
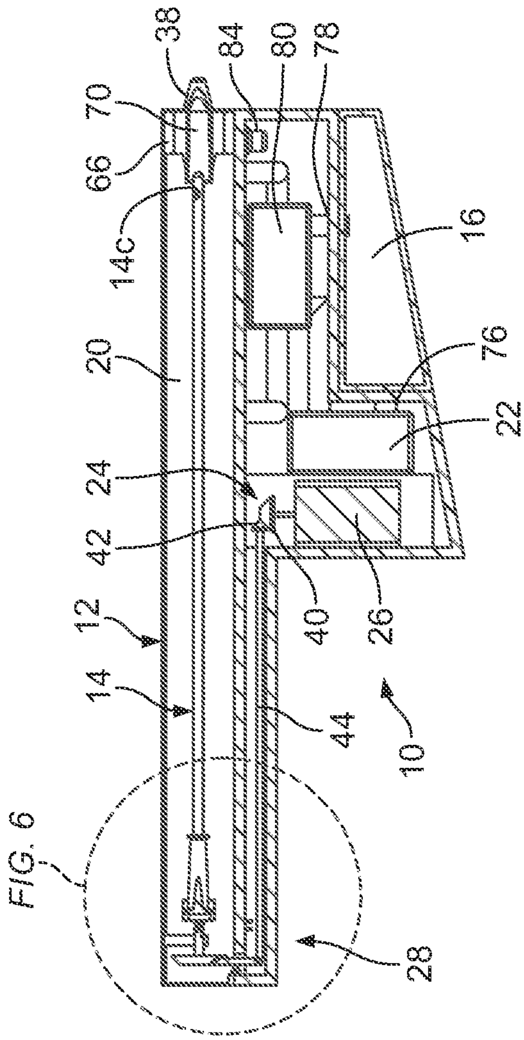
FIG. 5 is a cross-sectional top view of the smart meter at section 5-5 of FIG. 4, and noting a designated detail area shown in FIG. 6.
Figure 13:
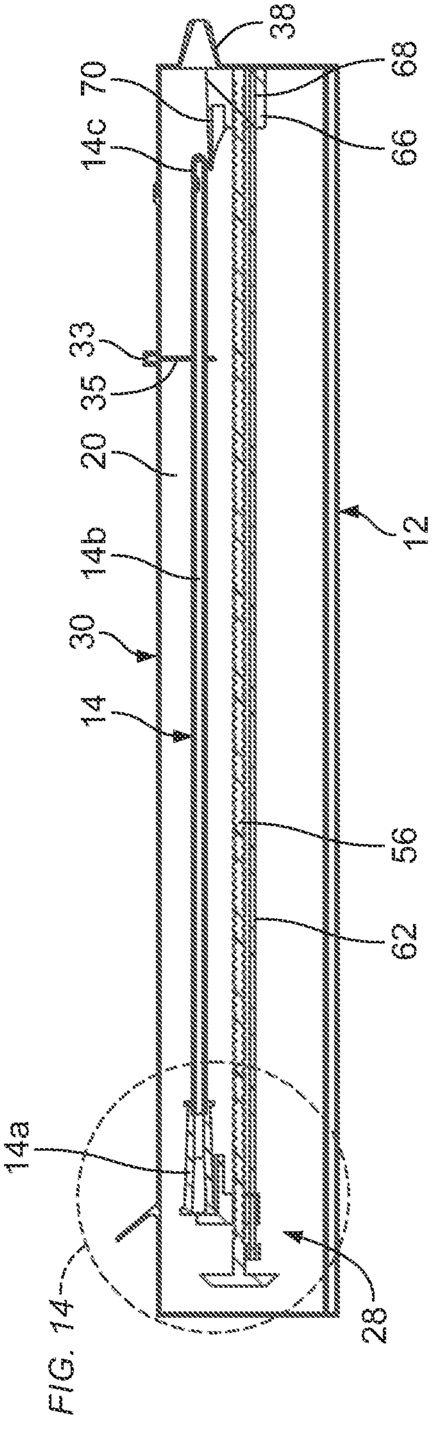
FIG. 13 is a cross-sectional side view of the catheter chamber portion of the smart meter at section 13-13 of FIG. 12, and noting an designated detail area shown in FIG. 14.
Figure 12:
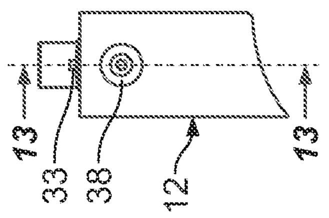
FIG. 12 is a front view of the catheter chamber portion of the smart meter of FIG. 1, identifying a section 13-13, which is shown in FIG. 13.

Prior to catheterization, a user may the lift tab 32 to open the lid 30 and insert a catheter 14 into the hydration chamber 20, in engagement with the carriage 58, as seen in FIGS. 5, 13 and 15. The smart meter 10 provides for hydration of the catheter 14 in the hydration chamber 20, to activate lubricant, such as a hydrophilic coating, provided on the catheter. For example, when the catheter 14 is a hydrophilic catheter, the smart meter 10 provides hydration or wetting of the hydrophilic coating of the catheter 14. Hydration may occur over a set period of time, such as 30 to 60 seconds (or shorter or longer as needed), during which de-ionized water, tap water or other suitable fluid serves as the fluid which is recirculated through the hydration chamber 20. The pump 22 may be of a peristaltic type and pumps fluid from the fluid reservoir 16 to the hydration chamber 20. It will be appreciated that other types of pumps may be used, such as diaphragm, centrifugal and positive displacement, etc. The pump 22 has a relatively low flowrate, such as 1 ml to 100 ml per minute and the flowrate may be monitored and controlled by a flowmeter.

The fluid hydrates the catheter 14 to activate a lubricant, such as a hydrophilic coating, on the catheter tip 14*c* and catheter shaft 14*b*, such as the hydrophilic coating. Flow from the fluid reservoir 16 through an inlet port 76 in the housing 12 and into the pump 22, as well as recirculation of the fluid in the hydration chamber 20, and flow back to the fluid reservoir 16 through an outlet port 78, may be controlled by a valve 80, such as a three-way valve that is connected to conduit therebetween. Alternatively, a pair of or single two-way valve(s) may be used to continuously recirculate fluid from the fluid reservoir 16 to the hydration chamber 20. The smart meter 10 also may be configured to optionally provide hydrating fluid injection through the introducer tip 38 to the catheter insertion site to supplement catheter lubricity provided by the hydration chamber. For example, 0.1-1.0 ml may be injected into the urethra, and the fluid may include a glycerol type of lubricant to supplement the catheter lubricity. As a further alternative, a lubricant may be added to the catheter at the point of insertion.

To ensure an authorized catheter 14 is being used with the smart meter 10, a catheter identification device 82 may be provided in the housing 12 or may be configured to be connected to the smart meter. In the first example smart meter 10, the catheter identification device 82 is shown in FIG. 6 as a bar code reader that reads a bar code applied to the catheter 14. If the bar code reader detects that the catheter is not one of a preapproved type, the smart meter 10 may indicate this to the user via the operator interface and controller 74.

It will be appreciated that the controller may be programmed to control all electronic functions, such as actuation of the catheter identification device 82, the speed of the pump 22, flowrate, opening and closing of the valve(s), introduction of any additional fluid at the insertion site, and the speed and direction of the motor 26. The controller also may provide for data reading, storage and display, via interaction with sensors that may provide data, such as temperature (via a thermocouple), flow (via a flowrate meter) and PH level of the fluid, and force of insertion and withdrawal, and time of insertion and withdrawal of the catheter. The controller also may provide instructional information to the user via the user interface, such as step by step instructions for use, troubleshooting information and the like. The controller additionally may provide options for manual or automated catheter insertion, with optional automated withdrawal if the insertion force exceeds a critical limit that indicates an incidence of high friction. The insertion force may be measured and monitored, for example, if the motor 26 is a small electromagnetic motor with a strain gauge, which may provide an indication of insertion force during a catheterization procedure.

The smart meter 10 advantageously also may provide for sterilization the catheter. For example, the hydration fluid in fluid reservoir 16 and pumped into the hydration chamber 20 may include a sterilizing agent, such as Hydrogen Peroxide solution or hypochlorous agent. Optionally, the smart meter 10 also may include a sterilization source 84. The sterilization source may include a sterilization fluid, or as shown in the first example, it may include an infrared radiation or ultraviolet radiation lamp. Alternative use of sterilization fluid may include Ethylene Oxide, Hydrogen Peroxide or the like, and may be provided in a replacement cartridge and circulated around a small tube or buffer area. Further safety and cleanliness may be provided by inclusion of a vibratory source. For example, the controller may activate an ultrasonic vibratory source at the distal end of the housing 12 to shake bacteria or microbes from the catheter 14 during the insertion cycle. Detection and warning of excessive insertion or withdrawal force also may be provided visually or audibly.

While permitting the option of automated insertion of a catheter may relieve difficulty and stress in otherwise handling a catheter during self-catheterization, it will be appreciated that additional advantageous features may be provided by the smart meter 10. For instance, it may be used with simple, low cost catheters and may not require sterilization of the entire smart meter 10. If sterilization is desired or required, it may be made with lightweight materials that may be sterilized using liquids. It also provides for a fully hydrated catheter at the point of insertion, with the option of providing additional lubrication to the catheter or at the point of insertion.

It will be appreciated that the smart meter 10 advantageously may be used by having a user place the housing 12 of the smart meter 10 on the user's lap or a stable surface. The user grasps the lift tab 32 and pulls to open the lid 30, exposing the hydration chamber 20. The user places a catheter 14 in the hydration chamber 20 and closes the lid 30. The user attaches the fluid reservoir 16 to the housing 12. The user then uses the operator interface and controller 74 to activate the hydration and insertion of the catheter. However, the smart meter 10 only will proceed if the catheter identification device 82 has scanned and accepted the catheter 14 as being appropriate for use with the smart meter 10. The catheter 14 then is hydrated and passed through the introducer tip 38 to complete insertion. As the catheter is advanced to and through the introducer tip 38, the sterilization source 84, such as a UV lamp, is used to further disinfect the catheter 14. Once inserted, the access hatch 31 may be opened to expose the catheter connector 14*a* for drainage purposes. Upon closing the access hatch 31, the smart meter 10 may be used to withdraw the catheter 14 in an automated or manual manner.

A second example smart meter 110 is shown in FIGS. 19-26. The smart meter 110 includes a housing 112 that receives a catheter 114, and a fluid reservoir 116 that connects to the housing 112. A catheter hydration chamber 120, a pump 122 and a drive system 124 are located within the housing 112. The pump 122 is in communication with the fluid reservoir 116 and the hydration chamber 120. The drive system 124 includes a motor 126 and a drivetrain 128 that engages and moves the catheter 114. It will be understood that the catheter 114 may be of different configurations but typically will include a connector 114*a*, such as in the form of a funnel, a catheter shaft 114*b* having a passage therethrough, and a catheter tip 114*c* having at least one aperture to permit fluid communication through the catheter 114 from the tip 114*c* to the connector 114*a*.

The housing 112 includes a cover or lid 130. The hydration chamber 120 is provided within the housing 112 and includes a proximal seal 120*a* and a distal seal 120*b*, each of which permits passage of the catheter tip 114*c* and catheter shaft 114*b* therethrough. A catheter 114 may be inserted into the housing 112 through an opening 134 in the proximal end of the housing 112, and the fluid reservoir 116 may be received in a recess 132 where it is connected to the housing 112. Thus, during normal use, the housing 112 of the second example smart meter 110 would not normally need to be opened. As with the first example smart meter 10, the fluid reservoir 116 for the second example smart meter 110 may be reusable and filled prior to use, or a disposable prefilled item. The fluid reservoir 116 may have a suitable volume, for instance a volume of 2 ml to 10 ml or more, but will depend upon the hydration mechanism utilized and the volume of the hydration chamber 120. The fluid reservoir 116 may be conveniently connected to or removed from the housing 112, such as by similar means to those use with the first example smart meter 10, or other suitable means of connection.

Similar to the first example smart meter 10, the housing 112 of the second example smart meter 110 also may have an introducer tip at a distal end of the housing and through which the distal end or tip 114*c* and catheter shaft 114*b* are extendable, so as to provide for insertion of the catheter 114 into the individual. The introducer tip may have similar advantageous features to those described for the introducer tip 38 of the first example, such as adjustability for different catheter and/or urethra sizes, and may be self-cleaning and/or used to provide supplemental hydration and/or lubrication at the site of catheter insertion.

Figure 25:
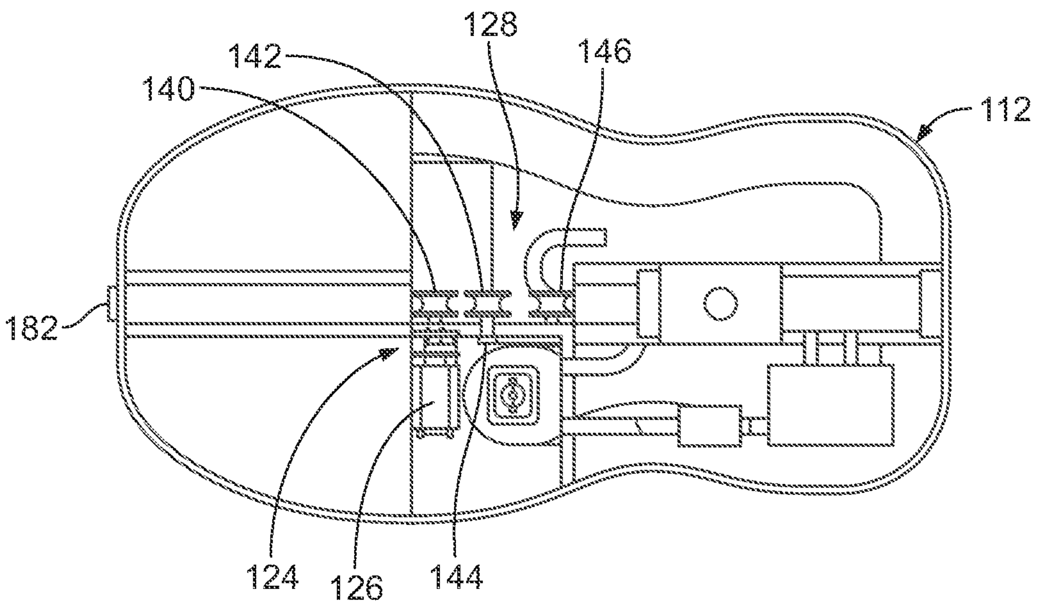
FIG. 25 is a top view of the smart meter of FIG. 19, without a catheter in the smart meter and with the front cover removed.
Figure 26:
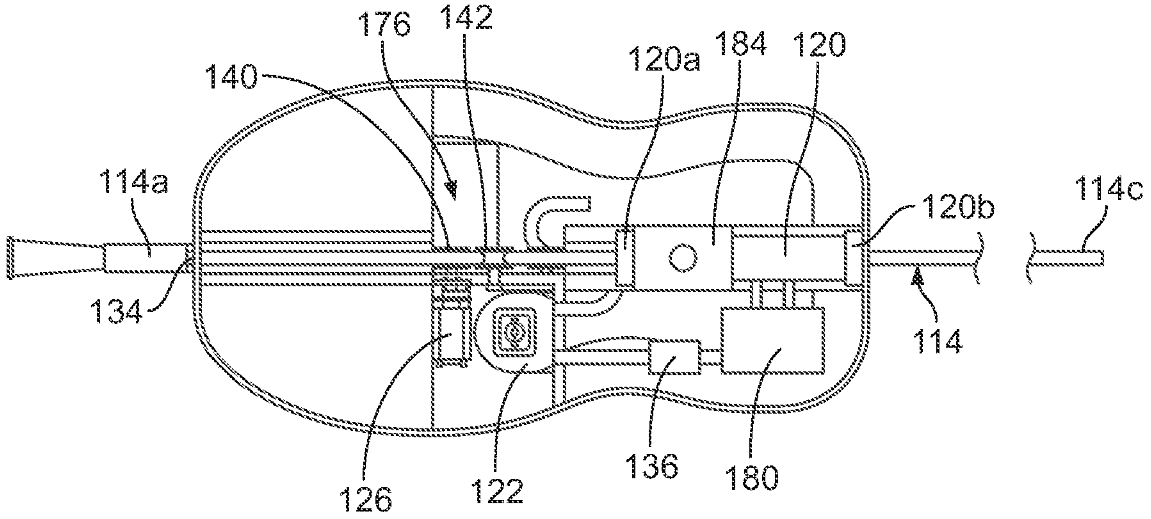
FIG. 26 is a top view of the smart meter of FIG. 19, with a catheter in the smart meter and with the front cover removed.

As may be appreciated in FIGS. 25-26, when in use for catheterization, the motor 126 and drivetrain 128 of the drive system 124 move the catheter 114 relative to the housing 112 in a first direction for catheter hydration and insertion and in an opposed second direction for catheter removal. In the example smart meter 110, the drivetrain 128 utilizes rotary motion to move the catheter 114. The rotary motion of the drivetrain 128 begins with a rotation of a drive pulley or roller 140 on the motor 126. The drive roller 140 rotates and engages the catheter shaft 114*b*. A second pulley or roller 142 is located on a spring loaded or biased arm 144 and provides assistance for the drive roller 140 to guide, grip and move the catheter shaft 114*b*. An idler pulley or roller 146 is provide distally of the second roller 142, and provides assistance in guiding the catheter tip 114*c* into the proximal seal 120*a* of the hydration chamber 120. Thus, the rotary motion of the drivetrain 128 includes rotation of a roller 140 that engages and moves a shaft 114*b* of the catheter 114.

The smart meter 110 includes a power source that may be held in a compartment 172 on the housing 112. As with the first example, the power source for the second example smart meter 110 may be in the form of one or more rechargeable batteries and may provide a similar function to that described for the first example. In the second example, the operator interface and controller are separated. As may be seen in seen in FIGS. 19 and 22-23, the operator interface 174 is located in the housing lid 130. The operator interface 174 includes input mechanisms 174*a*, such as membrane switches or buttons, and a readout, such as an LCD display 174*b*. Alternatives may be utilized, as discussed with respect to the first example smart meter 10. A controller 176 is located in the housing 112 and may include an onboard microprocessor or computer. It will be appreciated that the operator interface and controller may be configured as an integrated unit, or as shown in the second example as a separate operator interface and a controller. The operator interface 174 and controller 176 also may be programmed to utilize smart features, such as discussed with the first example smart meter 110, similar to smart handheld devices and may be configured to communicate with a separate device, such as a computer, tablet computer for cellular telephone.

Prior to catheterization, a user may insert a catheter tip 114*c* through the housing proximal opening 134 and advance the catheter tip 114*c* until it meets the drive roller 140 and second roller 142. The motor 126 may be activated to advance the catheter 114 until the catheter tip 114*c* is forced through the proximal seal 120*a* of the hydration chamber 120. The hydration and insertion cycle may be initiated, which causes the catheter 114 to be advanced further into and through the hydration chamber 120, and the catheter tip 114*c* continues to extend from the distal seal 120*b* as it is moves through the insertion cycle. Thus, the smart meter 110 provides for hydration of the catheter 114 in the hydration chamber 120, to activate hydrophilic coating of the catheter. As noted with the first example, hydration may occur over a set period of time, such as 30 to 60 seconds (or shorter or longer as needed), during which de-ionized water, tap water or other suitable fluid serves as the fluid which is recirculated through the hydration chamber 120. The pump 122 may be of a peristaltic type and pumps fluid from the fluid reservoir 116 to the hydration chamber 120. As with the first example, it will be appreciated that other types of pumps may be used. The pump 122 of the second example similarly has a relatively low flowrate, such as 1 ml to 100 ml per minute and the flowrate may be monitored and controlled by a flowmeter.

The fluid hydrates the catheter 114 to activate a lubricant, such as the hydrophilic coating, on the catheter tip 114*c* and catheter shaft 114*b*. Flow from the fluid reservoir 116 into the pump 122, as well as recirculation of the fluid in the hydration chamber 120, and flow back to the fluid reservoir 116, may be controlled by a valve 180, such as a three-way valve that is connected to conduit therebetween. As noted with respect to the first example, alternatively a pair of or single two-way valve(s) may be used to continuously recirculate fluid from the fluid reservoir 116 to the hydration chamber 120. The smart meter 110 also may be configured to optionally provide hydrating fluid injection through an introducer tip to the catheter insertion site to supplement catheter lubricity provided by the hydration chamber. As discussed with respect to the first example, 0.1-1.0 ml may be injected into the urethra, and the fluid may include a glycerol type of lubricant to supplement the catheter lubricity. As a further alternative, a lubricant may be added to the catheter at the point of insertion.

To ensure an authorized catheter 114 is being used with the smart meter 110, the smart meter includes a multi-pin connector 182 for connection to an auxiliary catheter identification device, such as a bar code reader that reads a bar code applied to the catheter 114. If the bar code reader detects that the catheter is not one of a preapproved type, the smart meter 110 may indicate this to the user via the display 174*b* of the operator interface 174, and the controller 176 may reject the catheter.

It will be appreciated that the controller 176 may be programmed to control all electronic functions, such as actuation of an auxiliary catheter identification device that is connected via multi-pin connector 182, the speed of the pump 122, flowrate, opening and closing of the valve(s), introduction of any additional fluid at the insertion site, and the speed and direction of the motor 126. The controller also may provide for data reading, storage and display, via interaction with a group of sensors 136 that may provide data, such as temperature (via a thermocouple), flow (via a flowrate meter) and pH level of the fluid, and force of insertion and withdrawal, and time of insertion and withdrawal of the catheter. The controller 176 also may provide instructional information to the user via the display 174*b*, such as step by step instructions for use, troubleshooting information and the like. The controller 176 may additionally provide options for manual or automated catheter insertion, with optional automated withdrawal if the insertion force exceeds a critical limit that indicates an incidence of high friction. The insertion force may be measured and monitored, for example, if the motor 126 is a small electromagnetic motor with a strain gauge, which may provide an indication of insertion force during a catheterization procedure.

The second example smart meter 110 advantageously also may provide for sterilization. For example, the hydration fluid in fluid reservoir 116 and pumped into the hydration chamber 120 may include a sterilizing agent. Optionally, the smart meter 110 may include another sterilization source 184. The sterilization source may include a sterilization fluid, or similarly to the first example, as shown in FIG. 26, it may include an infrared radiation or ultraviolet radiation lamp. Alternative use of sterilization fluid may include Ethylene Oxide, Hydrogen Peroxide or the like, and may be provided in a replacement cartridge and circulated around a small tube or buffer area. Further safety and cleanliness may be provided by inclusion of a vibratory source. For example, the controller may activate an ultrasonic vibratory source at the distal end of the housing 112 to shake bacteria or microbes from the catheter 114 during the insertion cycle. Detection and warning of excessive insertion or withdrawal force also may be provided visually or audibly.

While permitting the option of automated insertion of a catheter may relieve difficulty and stress in otherwise handling a catheter during self-catheterization, it will be appreciated that additional advantageous features may be provided by the smart meter 110. For instance, it may be used with simple, low cost catheters and may not require sterilization of the entire smart meter 110. If sterilization is desired or required, it may be made with lightweight materials that may be sterilized using liquids. It also provides for a fully hydrated catheter at the point of insertion, with the option of providing additional lubrication to the catheter or at the point of insertion.

It will be appreciated that the smart meter 110 advantageously may be used by having a user place the housing 112 of the smart meter 110 on the user's lap or a stable surface. The user inserts a catheter 114 through the proximal opening 134 in the housing 112 until it engages the drive roller 140 and second roller 142. The user attaches the fluid reservoir 116 to the housing 112 via insertion into the recess 132 of the housing lid 130. The user then uses the operator interface 174 and controller 176 to activate the hydration and insertion of the catheter. However, the smart meter 110 only will proceed if the catheter identification device that communicates with the smart meter 110 via the multi-pin connector 182 has scanned and accepted the catheter 114 as being appropriate for use with the smart meter 110. The catheter 114 then is passed through the hydration chamber 120 to be hydrated and passed through the distal hydration seal 120*b* to be presented for insertion into the individual. As noted previously, an introducer tip may be used for the second example smart meter 110 in a similar manner that that which was described for the first example smart meter 10. Also as the catheter is passed through the housing 112, the sterilization source 184, such as a UV lamp, is used to further disinfect the catheter 114.

Figure 28:
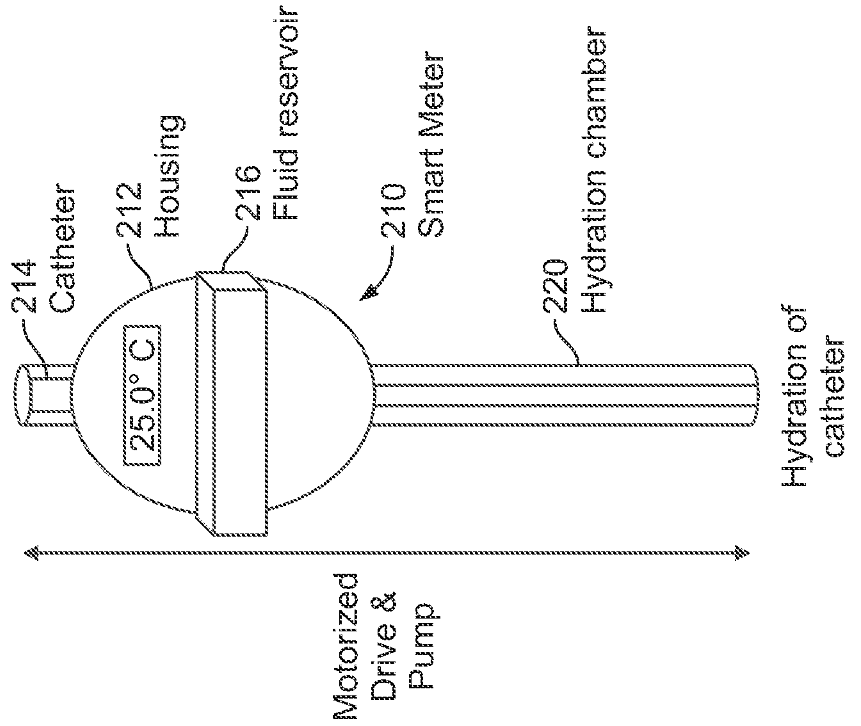
FIG. 28 is a simplified schematic representation similar to FIG. 27, but with a catheter having been hydrated in the smart meter and prior to insertion.
Figure 27:
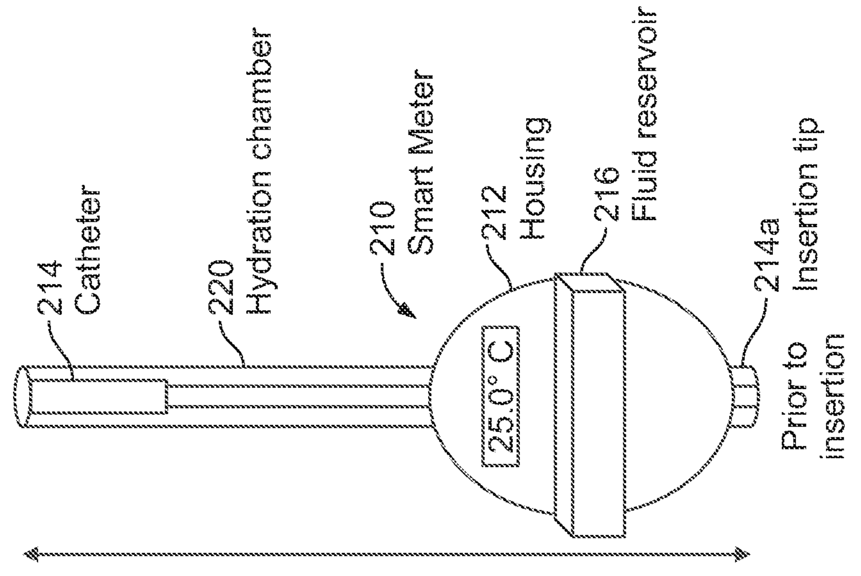
FIG. 27 is a simplified schematic representation of a third example smart meter, with a catheter in the smart meter and prior to catheter insertion.

Turning to FIGS. 27 and 28, a simplified schematic representation is shown to provide a third example smart meter 210. The third example may use many of the same features of the first and second smart meters 10, 110. The third example is presented to show yet a further configuration is possible, where the smart meter 210 includes a housing 212 that receives a catheter 214, and a fluid reservoir 216 that connects to the housing 212. A catheter hydration chamber 220, a pump and a drive system are located within the housing 212. The pump is in communication with the fluid reservoir 216 and the hydration chamber 220. The drive system includes a motor and a drivetrain that engages and moves the catheter 214. The pump, drive system and motor may be similar to or variations of those already described in the first and second examples, but in the third example, the entire hydration chamber 220 and catheter 214 move relative to the housing 212 during hydration of the catheter 214. This prepares the catheter 214 for insertion at its tip 214*a*, which is occurs after catheter hydration by advancing the catheter 214 distally from the hydration chamber 220.

Figure 29:
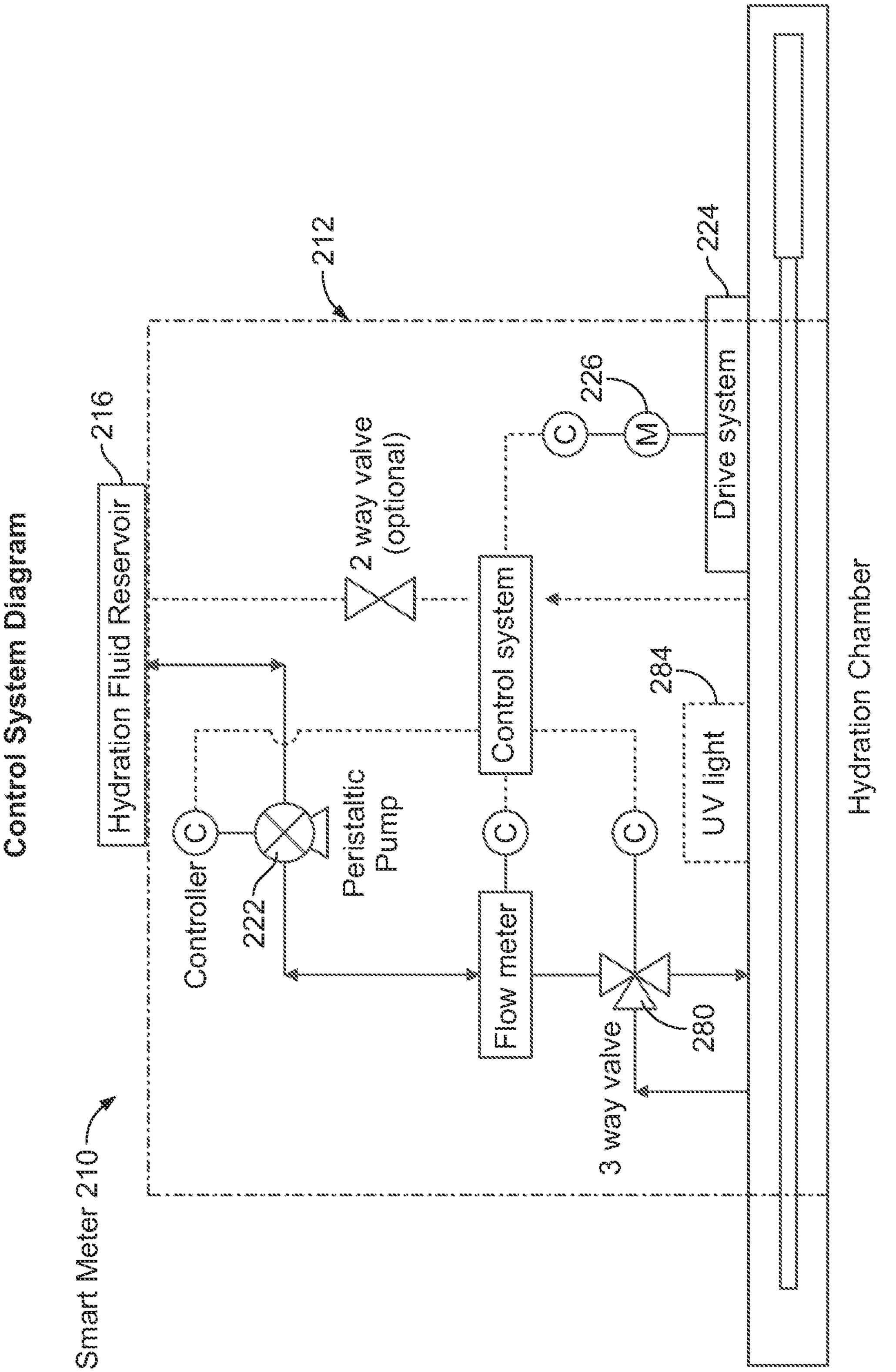
FIG. 29 is a process flow diagram showing interrelationships between portions of the third example smart meter shown in FIGS. 27-28.

FIG. 29 provides a control system diagram showing interrelationships between portions of the third example smart meter 210 shown in FIGS. 27-28. The diagram is not intended to show actual locations of the portions of the smart meter 210, but rather is intended to show the general network of inputs to the control system, which are utilized in completing the hydration and insertion functions of the third example smart meter 210. Thus, the diagram shows a fluid reservoir 216 that communicates with a pump 222, and the pump 222 is in communication with a valve 280 to provide recirculation of the fluid from the fluid reservoir 216 and through a hydration chamber 220 to hydrate the catheter 214. The fluid passes through a flowmeter 222*a* which provides useful information regarding the flowrate. A sterilization source 284 in the form of a UV light acts on the catheter 214 as it is advanced relative to the housing 212 and passes the sterilization source 284. A motor 226 of a drive system 224 is used to advance the catheter 214 relative to the housing 212. The control system is shown to highlight the interactions of the controller with the pump 222, the flowmeter, the valve 280 and the motor 226. The controller of this example uses these interactions to read and store data and to adjust the operation of the third example smart meter 210 to complete hydration and insertion of the catheter 214, as well as to move the catheter 214 in the opposite direction, so as to remove the catheter 214.

It should be understood that various modifications to the presently preferred embodiments described herein will be apparent to those skilled in the art. Such changes and modifications can be made without departing from the spirit and scope of the invention disclosed herein.

What is claimed is:

1. A smart meter for urinary catheter hydration and insertion, comprising: a housing that receives a urinary catheter; a fluid reservoir that connects to the housing; a urinary catheter hydration chamber, a pump and a drive system which are located within the housing; the pump is in communication with the fluid reservoir and the urinary catheter hydration chamber; and the drive system includes a motor and a drivetrain that engages and moves the urinary catheter, wherein the drive system moves the urinary catheter to advance and extend the urinary catheter from the housing for insertion into a user.

2. The smart meter for urinary catheter hydration and insertion of claim 1 wherein the drive system also moves the urinary catheter to remove the urinary catheter from the user.

3. The smart meter for urinary catheter hydration and insertion of claim 1 wherein the drivetrain utilizes rotary motion to move the urinary catheter.

4. The smart meter for urinary catheter hydration and insertion of claim 3 wherein the rotary motion of the drivetrain includes rotation of a roller that engages and moves a shaft of the urinary catheter.

5. The smart meter for urinary catheter hydration and insertion of claim 3 wherein the rotary motion of the drivetrain includes rotation of a screw drive assembly.

6. The smart meter for urinary catheter hydration and insertion of claim 5 wherein the screw drive assembly includes a screw shaft and a urinary catheter holder that engages and moves along the screw shaft.

7. The smart meter for urinary catheter hydration and insertion of claim 1 wherein the motor further comprises a strain gauge that measures insertion force.

8. The smart meter for urinary catheter hydration and insertion of claim 1 further comprising a power source.

9. The smart meter for urinary catheter hydration and insertion of claim 8 wherein the power source further comprises a rechargeable battery.

10. The smart meter for urinary catheter hydration and insertion of claim 1 wherein the pump is of a peristatic type and pumps fluid from the fluid reservoir to the urinary catheter hydration chamber.

11. The smart meter for urinary catheter hydration and insertion of claim 1 further comprising a sterilization source.

12. The smart meter for urinary catheter hydration and insertion of claim 11 wherein the sterilization source further comprises a sterilization fluid, infrared radiation, or ultraviolet radiation.

13. The smart meter for urinary catheter hydration and insertion of claim 1 further comprising a urinary catheter identification device.

14. The smart meter for urinary catheter hydration and insertion of claim 13 wherein the urinary catheter identification device further comprises a bar code reader that reads a bar code applied to the urinary catheter.

15. The smart meter for urinary catheter hydration and insertion of claim 1 further comprising a controller that controls the pump and the motor.

16. The smart meter for urinary catheter hydration and insertion of claim 15 wherein the controller further provides data reading, data storage, and instructional information.

17. The smart meter for urinary catheter hydration and insertion of claim 1 further comprising a vibratory source.

18. The smart meter for urinary catheter hydration and insertion of claim 1 further comprising an introducer tip at a distal end of the housing and through which a distal end of the urinary catheter is extendable for insertion into a urethra.

19. The smart meter for urinary catheter hydration and insertion of claim 18 wherein the introducer tip is adjustable to accommodate urinary catheter shafts of different diameters.

20. The smart meter for urinary catheter hydration and insertion of claim 18 wherein the introducer tip is used to provide hydrating fluid injection to the urethra to supplement urinary catheter lubricity provided by the urinary catheter hydration chamber.

* * * * *